(12) United States Patent
Von Schuckmann

(10) Patent No.: US 10,010,687 B2
(45) Date of Patent: Jul. 3, 2018

(54) DEVICE FOR INHALING POWDERY SUBSTANCES

(71) Applicant: Alfred Von Schuckmann, Kevelaer (DE)

(72) Inventor: Alfred Von Schuckmann, Kevelaer (DE)

( * ) Notice: Subject to any disclaimer, the term of this patent is extended or adjusted under 35 U.S.C. 154(b) by 508 days.

(21) Appl. No.: 14/389,036

(22) PCT Filed: Apr. 9, 2013

(86) PCT No.: PCT/EP2013/057344
§ 371 (c)(1),
(2) Date: Sep. 29, 2014

(87) PCT Pub. No.: WO2013/156339
PCT Pub. Date: Oct. 24, 2013

(65) Prior Publication Data
US 2015/0059747 A1    Mar. 5, 2015

(30) Foreign Application Priority Data

Apr. 20, 2012  (DE) .......................... 10 2012 103 482

(51) Int. Cl.
*A61M 15/00*  (2006.01)

(52) U.S. Cl.
CPC ...... *A61M 15/0041* (2014.02); *A61M 15/003* (2014.02); *A61M 15/004* (2014.02);
(Continued)

(58) Field of Classification Search
CPC ............ A61M 15/004; A61M 15/0025; A61M 15/0026; A61M 15/003; A61M 15/0035;
(Continued)

(56) References Cited

U.S. PATENT DOCUMENTS 5,685,294 A * 11/1997 Gupte ............... A61M 15/0028
                                                                                   128/203.15
6,606,992 B1    8/2003 Schuler et al.
(Continued)

FOREIGN PATENT DOCUMENTS

DE    10 2006 010 089 A1    10/2007
DE    10 2010 016 549 A1    10/2011
(Continued)

OTHER PUBLICATIONS

Machine Translation of patent DE102010016549, Alfred Von Shuckmann, Oct. 2011.*
(Continued)

*Primary Examiner* — Valerie L Woodward
(74) *Attorney, Agent, or Firm* — Collard & Roe, P.C.

(57) ABSTRACT

A device for inhaling powdery substances, in particular of a medical nature, contained in capsules, can be brought into an emptying position via a receptacle that can be moved in a flat housing, in which position the capsule wall can be pierced via movable needles for the purpose of sucking out the capsule content through a mouthpiece channel, which extends in axial extension of the capsule chamber. The receptacle is designed as a part of the narrow lateral wall of the flat housing that can be pivoted out to a limited extent about an axis and a partial region of the narrow lateral wall plane is designed as a spring-loaded push-button for the needle bearings, in such a way that the partial region moves back to the plane of the narrow lateral wall at a maximum.

5 Claims, 8 Drawing Sheets

(52) U.S. Cl.
CPC .... *A61M 15/0025* (2014.02); *A61M 15/0026* (2014.02); *A61M 15/0028* (2013.01); *A61M 15/0035* (2014.02); *A61M 2202/064* (2013.01); *A61M 2206/16* (2013.01)

(58) Field of Classification Search
CPC .......... A61M 15/0041; A61M 15/0028; A61M 15/0033; A61M 15/008; A61M 15/0021; A61M 15/0036; A61M 15/0038; A61M 15/0043; B65D 51/002
See application file for complete search history.

(56) References Cited

U.S. PATENT DOCUMENTS

| | | | | |
|---|---|---|---|---|
| 8,539,946 | B2 * | 9/2013 | Esteve | A61M 15/0028 128/203.15 |
| 8,746,244 | B2 | 6/2014 | Kaemper et al. | |
| 2005/0279357 | A1 * | 12/2005 | Wachtel | A61K 9/0073 128/203.15 |
| 2008/0105256 | A1 * | 5/2008 | Lulla | A61M 15/0028 128/203.21 |
| 2011/0120463 | A1 * | 5/2011 | Esteve | A61M 15/0028 128/203.15 |
| 2011/0232637 | A1 * | 9/2011 | Kaemper | A61M 15/0028 128/203.12 |
| 2013/0186398 | A1 * | 7/2013 | Baillet | A61M 15/0028 128/203.15 |
| 2013/0255679 | A1 * | 10/2013 | Andrade | A61M 15/0028 128/203.15 |

FOREIGN PATENT DOCUMENTS

| | | | | |
|---|---|---|---|---|
| DE | 102010016549 | A1 * | 10/2011 | ........ A61M 15/0028 |
| WO | 2011/039307 | A2 | 4/2011 | |

OTHER PUBLICATIONS

International Search Report of PCT/EP2013/057344, dated Jul. 8, 2013.

* cited by examiner

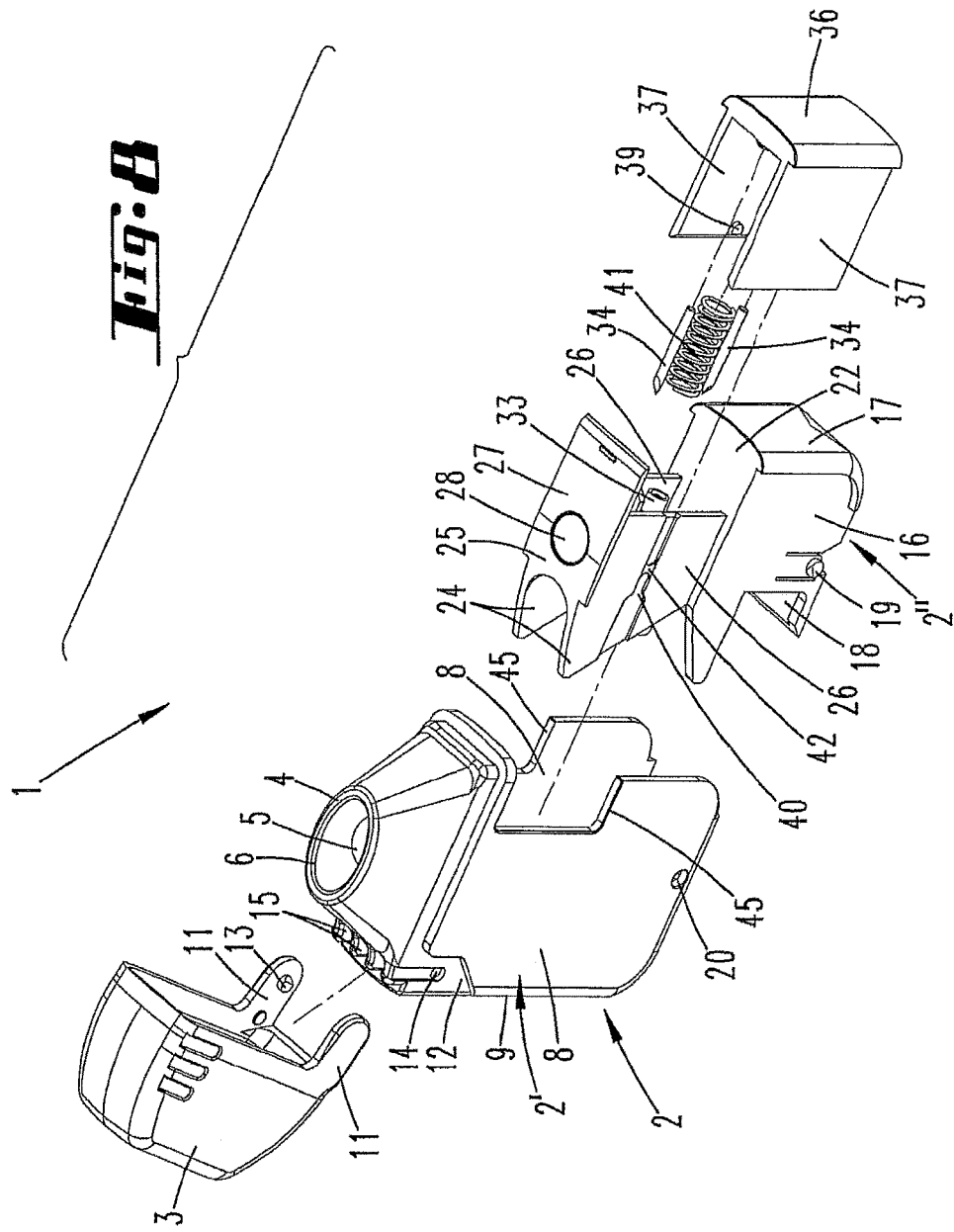

DEVICE FOR INHALING POWDERY SUBSTANCES

CROSS REFERENCE TO RELATED APPLICATIONS

This application is the National Stage of PCT/EP2013/057344 filed on Apr. 9, 2013, which claims priority under 35 U.S.C. § 119 of German Application No. 10 2012 103 482.6 filed on Apr. 20, 2012, the disclosure of which is incorporated by reference. The international application under PCT article 21(2) was not published in English.

The invention relates to a device for inhaling pulverulent substances, in particular of a medicinal type, contained in capsules which can be moved into an emptying position by means of a receptacle which is movable in a flat housing, in which position the capsule wall can be penetrated by means of displaceable needles for the purposes of evacuating the capsule contents through a mouthpiece duct which extends as an axial extension of the capsule chamber.

Devices of the type in question are known, for example also by the term 'capsule inhalers'. These are predominantly used to inhale medicinal, pulverulent compounds, which are further divided into portions in capsules. Generally, capsules of this type consist of two parts, namely a capsule body and a capsule cap, which are slid into one another in a telescopic manner, wherein, in particular in order to carry inhalable substances, capsules consist of either a plastics material having very low water absorbency or alternatively of gelatine. DE 10 2010 016549 A1 discloses a device of the type in question. In this device, the capsule carrying the substance to be inhaled is placed in a capsule chamber by means of a slide to be moved manually by the user. When in the position for receiving the capsule, said slide protrudes beyond the narrow side wall of the flat housing. By manually moving the slide towards the housing interior, the capsule is moved into an inhalation-preparatory position, in which the capsule chamber which receives the capsule is present as an axial extension of the mouthpiece duct. In the slide comprising the capsule chamber there is arranged an additional button-like slide which is movable in the same movement direction and the actuation surface of which, in order to be acted upon, protrudes beyond the narrow side wall of the housing even when the device is in the non-use position. By moving the button-like slide further, the capsule wall is pierced by needles fixed to said button-like slide, this piercing taking place by overcoming the spring force which forces the needles and the button-like slide back into an unloaded position. For inhalation, the needles and the button-like slide are moved back into their spring-loaded normal position.

In a device known from DE 10 2006 010 089 A1, the receptacle for a capsule is provided such as to be able to open out on the side of a wide side of the device. The needles for piercing are provided independently of the receptacle and can be actuated in the vertical direction of the device. WO 2011/039307 A2 also discloses a device of this type, in which the needles are fastened in a lateral button; the receptacle, however, can be loaded in the device from above independently thereof.

Proceeding from the aforementioned prior art, the problem addressed by the invention is that of providing a device of the stated type, which is advantageous in terms of user-friendly operation and use of the device.

This problem is solved by the subject matter of the invention, the basis of which is formed by the receptacle being formed about an axis as a part of a narrow side wall of the flat housing that can pivot out in a limited manner, and a portion of a narrow side wall plane being formed as a spring-mounted button for needle bearings, in which the needles are mounted, such that the portion is set back at most as far as into the plane of the narrow side wall and the button and the button is guided in the outwardly pivotable housing part in a manner limited by a stop. As a result of this configuration, the device is designed such that it is closed on all sides in particular when in the unloaded normal position, i.e. also in particular in the non-use position. In said non-use position, the part comprising the receptacle is pivoted in inside the flat housing, said part forming at least a portion of the narrow side wall, in particular when the device is in the non-use position, which narrow side wall preferably extends parallel to an opposite narrow side wall. The spring-mounted button, which is movable in particular in a slide-like manner and intended for moving the needles into a position in which they pierce the capsule in the capsule chamber, does not project out beyond the plane of the narrow side wall when in the normal position when in particular not loaded by the user. Instead, the portion forming the button is merely set back at most as far as into the plane of the narrow side wall. The preferably overall closed design, thereby achieved, of the device provides particular advantages when the device is carried in a pocket or the like, for example in a jacket pocket or trousers pocket, in particular when said device is in the position in which the mouthpiece is closed by a cap, as is more preferable. When the device is in this storage position, preferably all the openings of the device that are relevant for ventilation are closed by housing portions and/or by a cap which in particular covers the mouthpiece at the same time, whereby for example dust or dirt particles are prevented from entering in particular the air inlet or also the capsule chamber.

In a preferred embodiment, the device thus comprises a handy, approximately palm-sized flat housing which allows for favourable operation of the device. In this case, in terms of a cross section, a width-depth ratio of the flat housing of preferably 2:1 is provided. The height of the device including a cap, which is preferably provided and covers the mouthpiece, is preferably 3 to 5 times the width as viewed transverse thereto. The part which forms the receptacle and can pivot outwards in a limited manner can more preferably pivot about a pivot axis which extends transverse to the width direction of the flat housing. If the cap which covers the mouthpiece when the device is in the non-use position is likewise pivotally arranged in a captive manner on the flat housing, as is more preferable, in a preferred embodiment the pivot axis thereof extends parallel to the pivot axis of the part comprising the receptacle.

More preferably, when the receptacle is in the open position, the insert cross section of the capsule chamber is stopped in an acute-angled stop position. Accordingly, the part, which forms the receptacle, of the narrow side wall of the flat housing can preferably be brought into an acute-angled position relative to a plane extending parallel to the narrow side wall of the flat housing, so as to thus expose the capsule chamber so it can be loaded with a capsule. This outwardly pivoted position is limited by a stop, as is also more preferable with the inwardly pivoted position. In this case, in the outwardly pivoted position, an acute angle of from 15 to 60°, more preferably of from 30 to 45°, is assumed, in particular of a central axis, which passes through the capsule chamber in the longitudinal direction, relative to a plane defined by the narrow side wall in the non-use position. The capsule chamber is thus located in a position which can be conveniently accessed by a user and in which a new capsule can accordingly be loaded or an empty capsule can be removed.

It is also preferably provided that the narrow side wall pivots out together with approximately one half of a box-shaped housing part, including a bottom part which has the pivot pin. Here, the pivot pin preferably acts together with the other half of the in particular box-shaped housing part, which is stationary relative to the outwardly pivotable part. In this case, the outwardly pivotable part can more preferably be inwardly pivoted into the substantially stationary housing part in a drawer-like manner, more preferably said outwardly pivotable part is accordingly flanked on either side by housing walls of the substantially stationary housing part.

In addition, the spring-mounted button is preferably guided in an interlocking manner into a position in which the button is located in a plane with the rest of the region of the narrow side wall. As a result, a substantially flat configuration of the associated narrow side wall is advantageously achieved overall when the device is in the normal position, i.e. when the one housing part is in the inwardly pivoted position and the button is in the normal position not loaded from the outside. This is achieved in particular by the button being guided in an interlocking manner and in a manner limited by a stop in the region of the outwardly pivotable housing part. Here, the spring acting on the button forces the button against the provided stop of the interlocking guide. Targeted movement of the button having the needles arranged thereon in the direction of the capsule wall piercing position can also be achieved thereby.

In terms of the disclosure, the ranges, ranges of values or ranges of multiples given above and below also include all intermediate values, in particular in increments of 1 or 10 of the respective dimension, where appropriate also without a dimension, in particular 1.01 times etc., in order to give the stated range limits an upper and lower limit, on the one hand, but alternatively or additionally, also with regard to the disclosure of one of more singular values from the range stated in each case.

The invention is described below on the basis of the accompanying drawings which, however, show just one embodiment and in which:

FIG. 8 is a perspective exploded view of the device.

Figure 1:
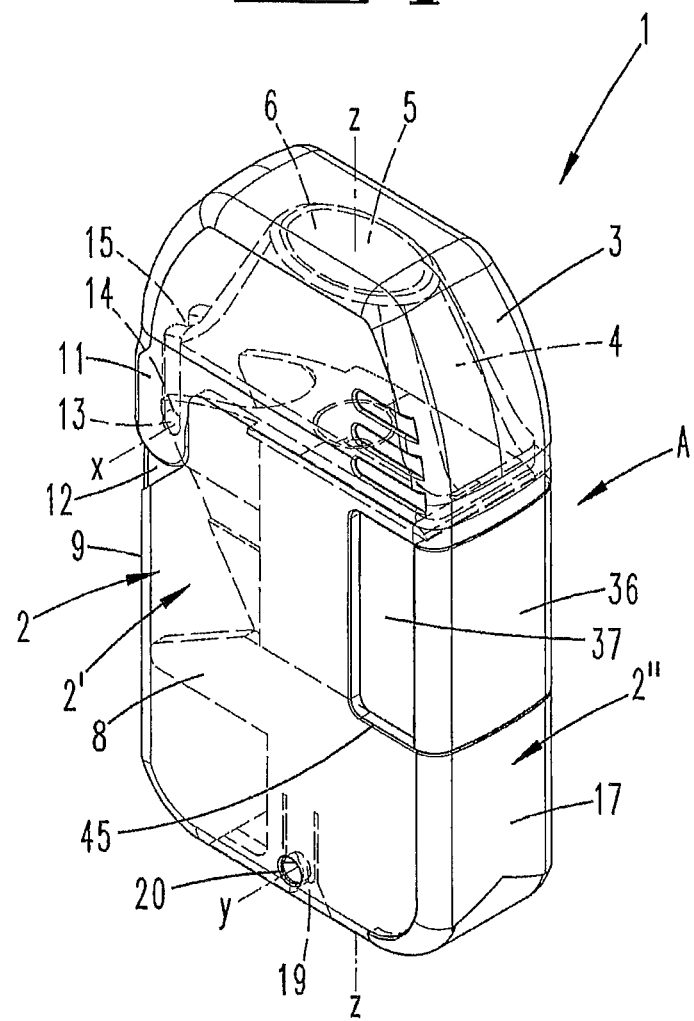
FIG. 1 is a perspective view of the device, said view relating to a non-use position with a closed cover.
Figure 2:
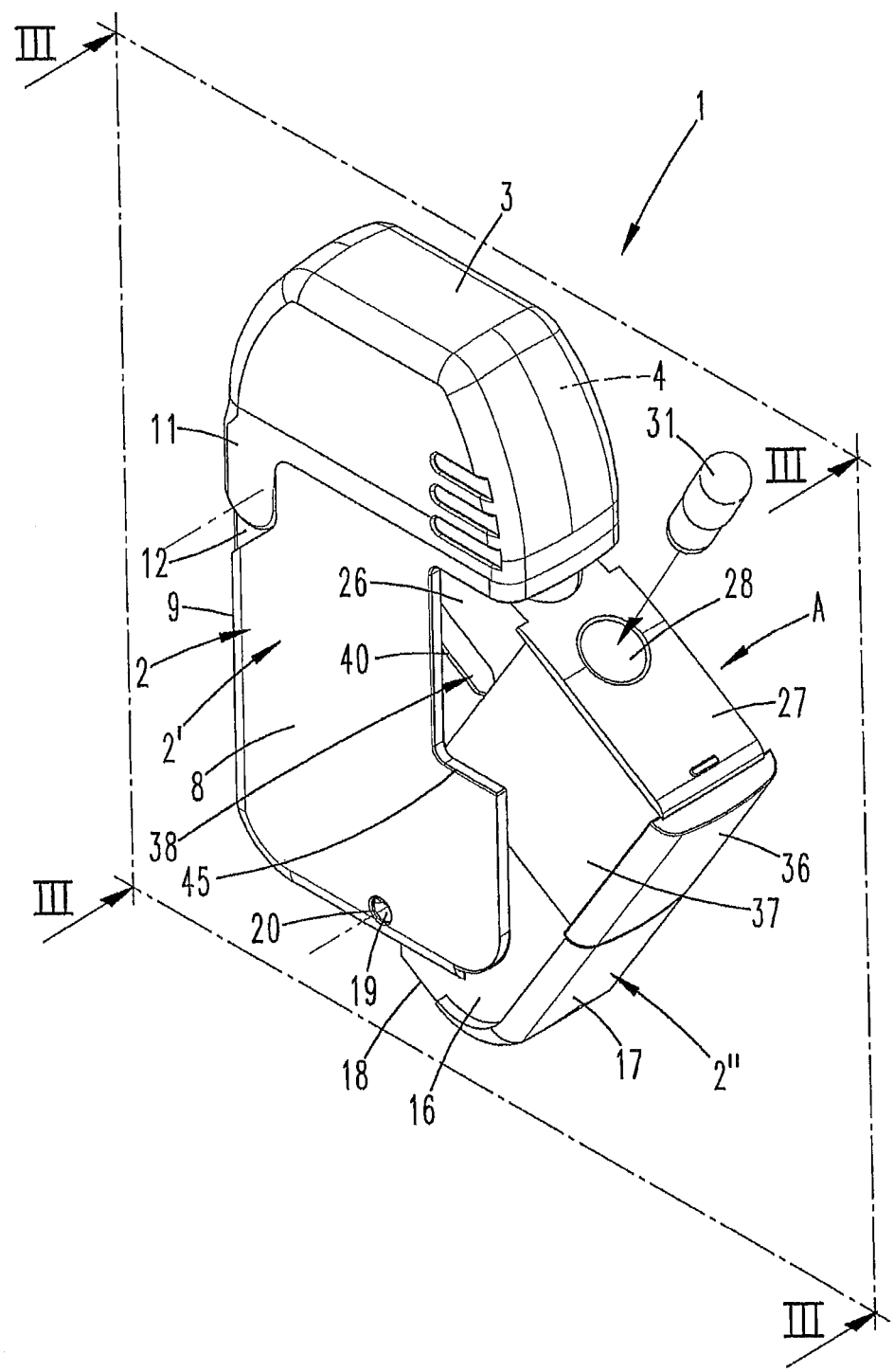
FIG. 2 is a perspective view of the device according to FIG. 1, said view, however, relating to the use-preparatory position.

With reference to FIG. 1, there is first shown and described a device 1 for inhaling pulverulent substances in the form of a capsule inhaler, which device 1 is produced as a pocket unit which can be comfortably carried.

The device 1 comprises a substantially two-part flat housing 2, for example having a housing part 2' which remains virtually stationary, in particular by being grasped by the hand, and a housing part 2" which is pivotally movable relative to said housing part 2'.

A cover-like cap 3 is hinged to the housing 2, more particularly to the stationary housing part 2'.

Figure 3:
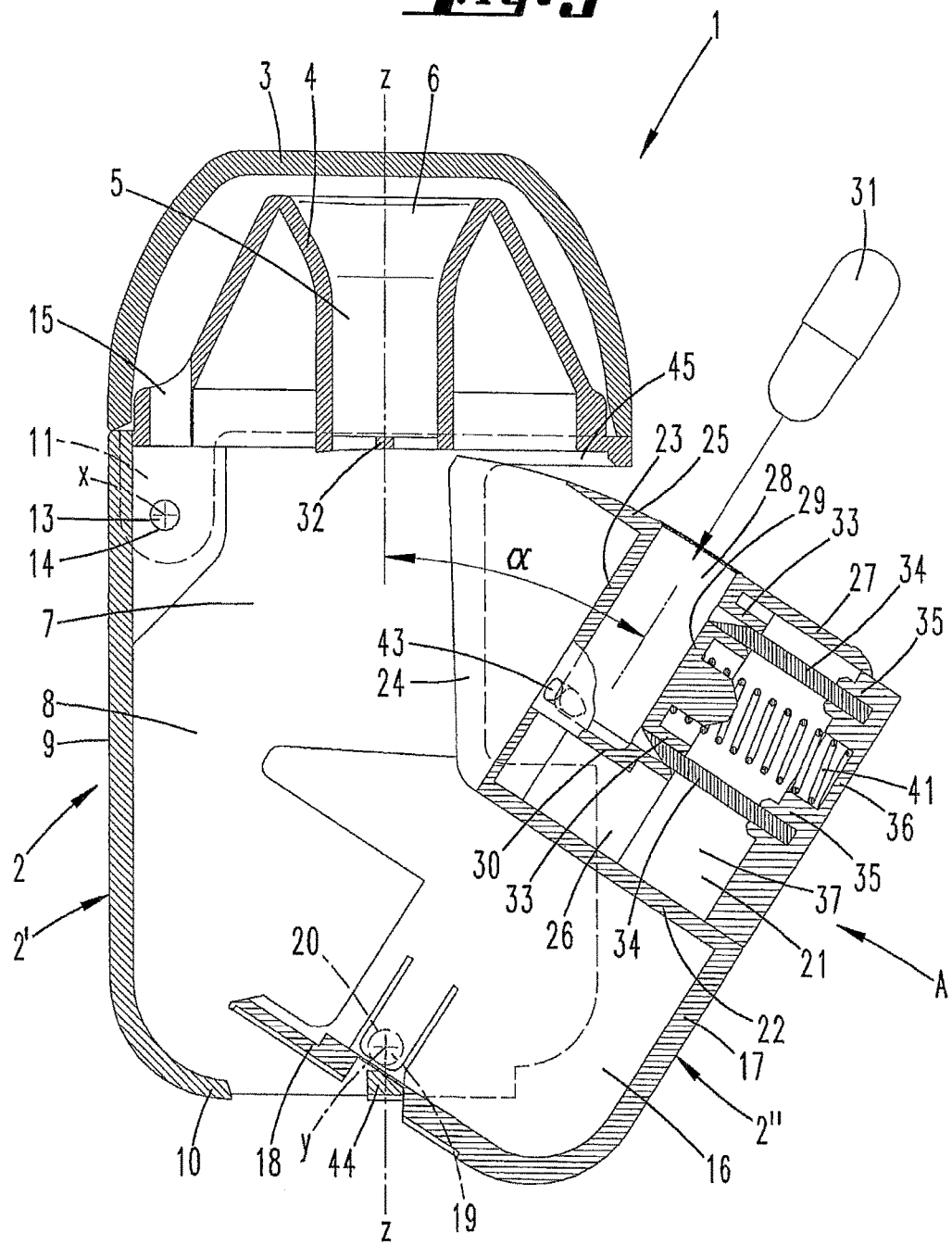
FIG. 3 is the section according to the sectional plane III in FIG. 2.

When the cap is in the closed position, also in a non-use position according to FIG. 1, the device 1 has a width-height ratio of approximately 1:2 and a depth which, when viewed perpendicularly to the height extension, i.e. also perpendicularly to the drawing plane for example in FIG. 3, approximately corresponds to half the size of the width extension of the housing 2. The parts of the device 1 are preferably produced as plastics moulded parts.

The housing 2, in particular the stationary housing part 2', first forms a mouthpiece 4 which, when viewed in the width direction of the housing 2, is arranged approximately in the centre and rises in the vertical direction of the housing 2 opposite housing walls of the stationary housing part 2' which are adjacent on either side, so that the mouthpiece 4 can be comfortably surrounded by the lips.

A mouthpiece duct 5, which extends vertically in terms of the drawings, opens in the mouthpiece 4 in the region of a mouthpiece outlet 6 which is open to the outside. In this case, the mouthpiece duct 5, starting from the mouthpiece outlet 6, preferably extends over almost a third of the vertical height of the device 1 and terminates opposite the mouthpiece outlet 6 freely in a space 7 formed in the housing 2. Said space is delimited substantially laterally by the wide side wall 8 of the stationary housing part 2' and of the narrow side wall 9 which delimits the wide side walls 8 at one end. Said narrow side wall preferably transitions into a bottom-part portion 10 opposite the mouthpiece 4.

Figure 5:
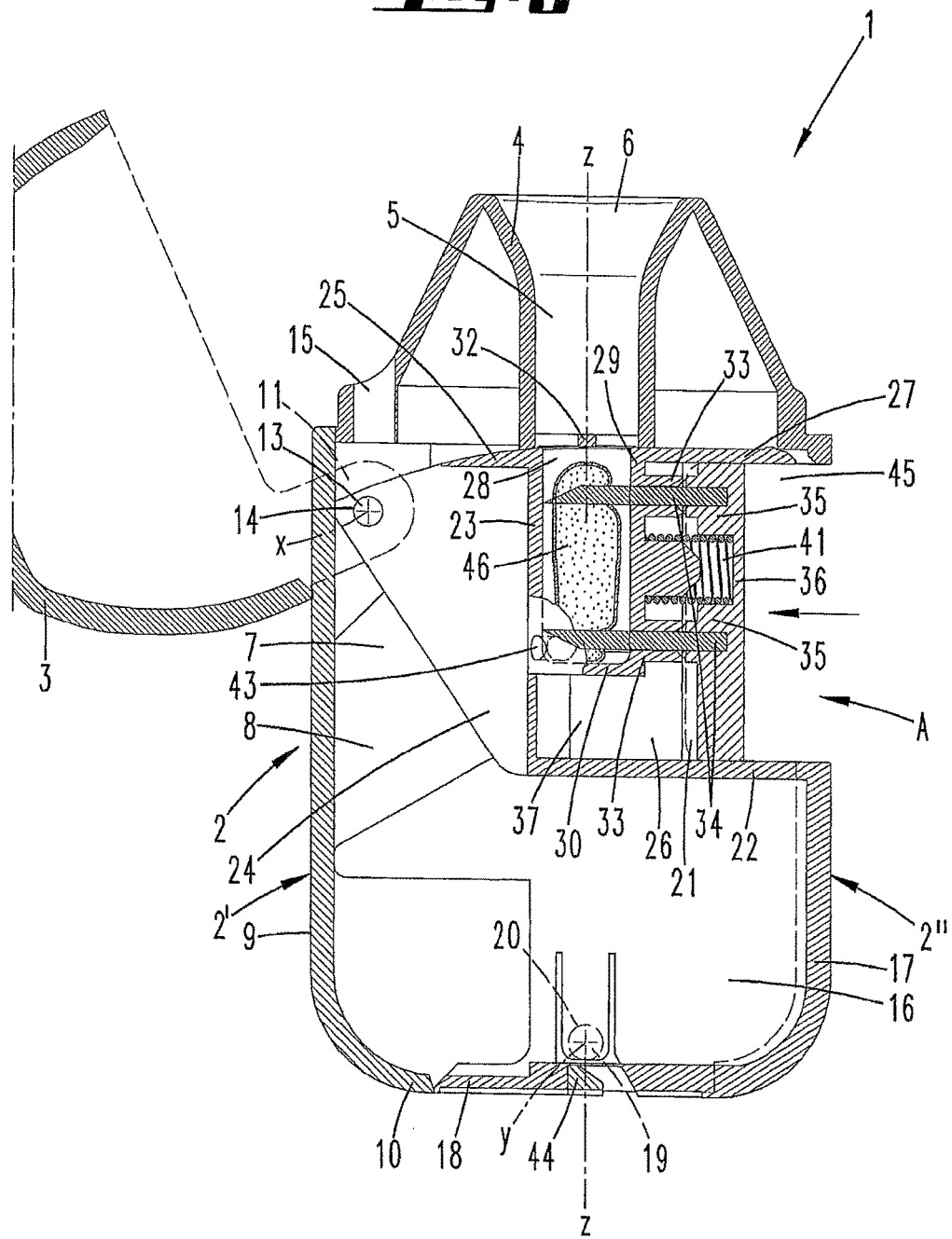
FIG. 5 is a subsequent view to FIG. 4 after a cap covering a mouthpiece has been pivoted away and an air inflow opening has been exposed, and in the course of a piercing operation of a capsule, received in the capsule chamber, as a result of a sliding movement of a narrow side wall portion.
Figure 6:
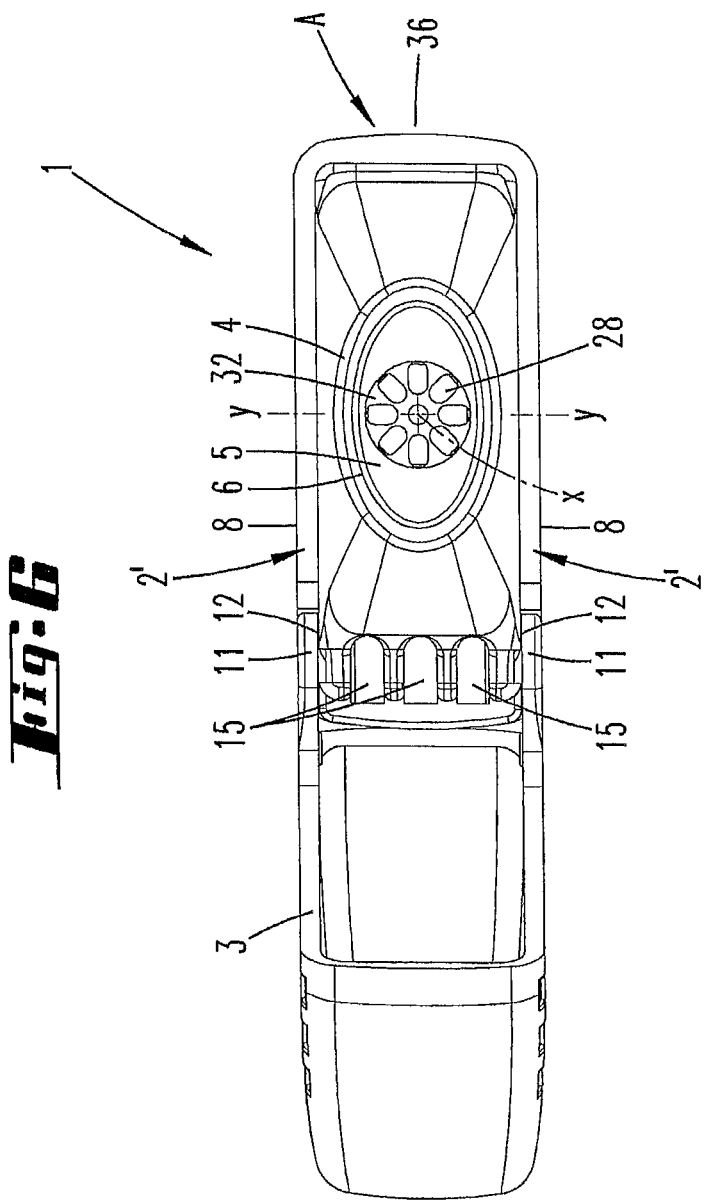
FIG. 6 is the plan view of the device with the cap pivoted away.
Figure 7:
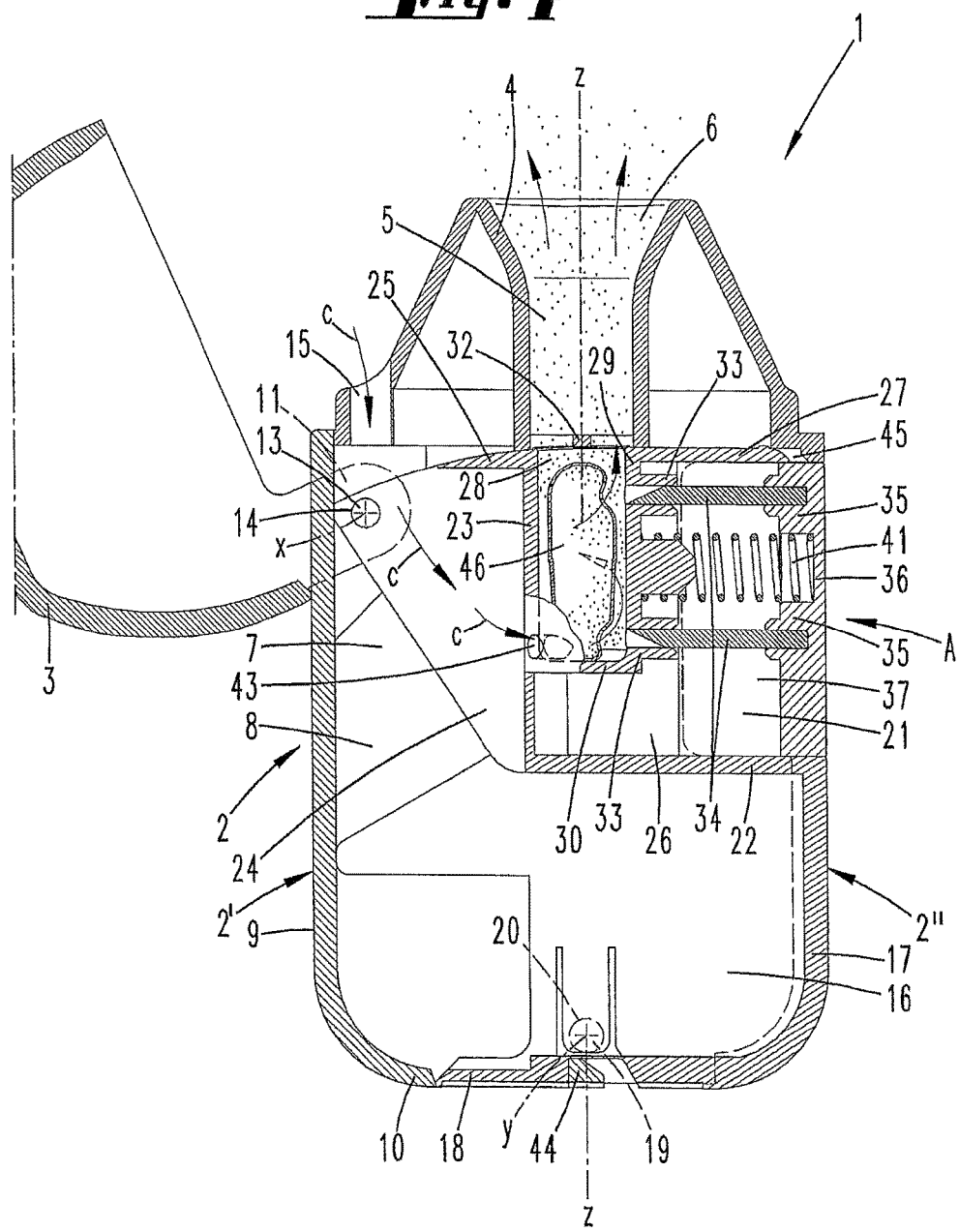
FIG. 7 is a subsequent view to FIG. 5 after the part of narrow side wall that supports the needles has been moved back, said view relating to the inhalation operation.

The cap 3 is hinged to the stationary housing part 2' so as to turn towards the narrow side wall 9. For this purpose, the cap 2 comprises two opposing tabs 11 which extend substantially vertically downwards and engage in correspondingly associated surface recesses 12 in the wide side walls 8. On the inner side of the walls, i.e. facing the respective wide side wall 8, the tab 11 is provided with a journal 12 for engaging in a corresponding, preferably blind-hole-like journal socket 14. The pivot axis x of the cap 3 accordingly extends in the depth direction of the housing 2, it preferably being made possible for the cap 3 to pivot away outwards as far as into a position which is limited by a stop and in which a cap wall hits the outer face of the facing narrow side wall 9 (see FIG. 5).

The device 1 comprises an air inlet opening 15 also facing the narrow side wall 9 of the stationary housing part 2'. When viewed in the width direction of the housing 2, said opening is adjacent to and axially offset from the mouthpiece 4, this offset being towards the narrow side wall 9 and approximately half the size of the axial extension of the mouthpiece duct 5. The air inlet opening 15 transitions into the aforementioned space 7.

When the cap is in the closed position according to FIG. 1, the cap 3 covers both the mouthpiece 4, having the mouthpiece outlet 6, and the air inlet opening 15. Accordingly, when the device 1 is in the non-use position, no dirt can enter the interior of the device 1 in particular through the mouthpiece 4 and/or the air inlet opening 15.

The stationary housing part 2' forms substantially half a box-shaped housing portion which opens in particular towards the side facing away from the narrow side wall 9 and more preferably also substantially towards the bottom of the housing. The housing part 2", which is pivotable with respect to the fixed housing part 2', preferably forms the other half of the box-shaped housing portion, which in this case in particular comprises two wide side walls 16 and a narrow side wall 17 which connects the two wide side walls 16.

The distance between the narrow side walls 16, which also extend parallel to one another as with the housing part 2', corresponds, in terms of the outwardly pointing faces thereof, substantially to the clearance between the inner faces, which point towards one another, of the wide side walls 8 of the housing part 2'. The extension of the narrow side wall 17, when viewed in the depth direction with regard to the drawings, preferably substantially corresponds to the opposite narrow side wall 9 of the housing part 2', which opposite narrow side wall extends in parallel when the device 1 is in the non-use position, whereby the narrow side wall 17 formed on the pivotable housing part 2" interacts with the associated vertical rim edges of the wide side walls 8 of the stationary housing part 2' in the manner of a limit stop.

In addition, the pivotable housing part 2" comprises an integrally formed bottom part 18, which, together with the bottom-part portion 10 of the fixed housing part 2', completes the bottom of the device 1 or the housing 2 when the device 1 is in the non-use position.

In the region of the bottom part 18, outwardly projecting pivot pins 19 are integrally formed on the outside of the wide side walls 16 and engage in correspondingly positioned and dimensioned recesses 20 or through-openings in the region of the inner sides, which face one another, of the wide side walls 8 of the stationary housing part 2'. The resulting pivot axis y of the housing part 2' accordingly extends preferably parallel to the pivot axis x of the cap 3.

A slide space 21 is formed in the pivotable housing part 2" which overall forms a receptacle A. With regard to a vertical cross section, said slide space is substantially rectangular to square. The slide space 21 comprises a slide space bottom 22 extending between the inner sides of the wide side walls 16. Said bottom, facing the narrow side wall 17, is connected to said narrow side wall.

Figure 4:
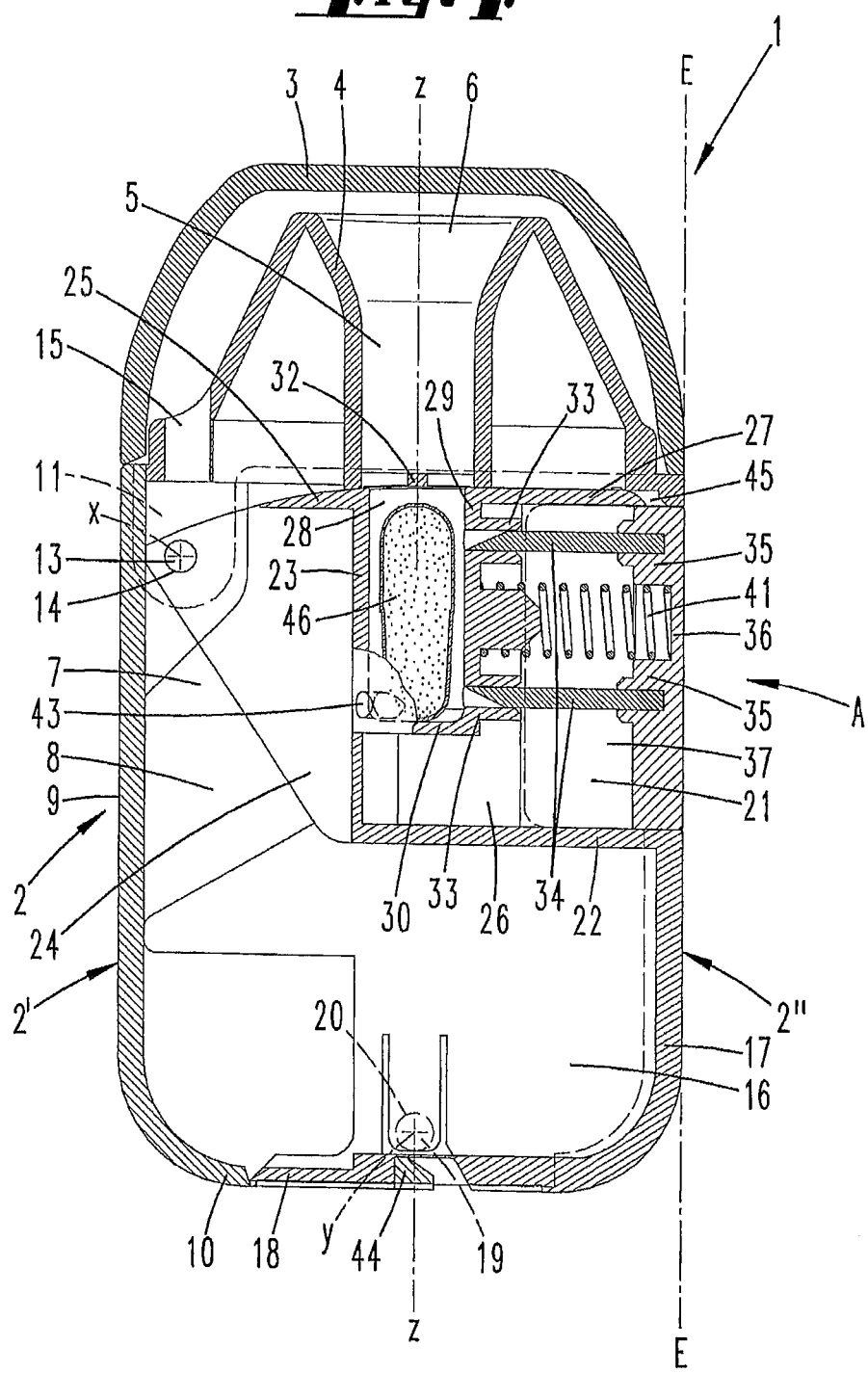
FIG. 4 is a sectional view corresponding to FIG. 3, relating to the position for moving a housing part comprising the capsule chamber into the inhaling position.

The slide space bottom 22 extends from this attachment region on the narrow side wall 17 into the space 7 preferably in parallel with the bottom of the housing 2 or in transverse alignment with a body axis z which preferably passes through the centre of the device 1. At the end, a slide space wall 23, which is oriented vertically when the device 1 is in the normal position, is formed on the slide space bottom 22. The rim edge, pointing vertically upwards, of said slide space wall hits an associated lower rim portion of the mouthpiece duct 5 when in the normal position according to FIG. 4.

The slide space 21 thus formed is open substantially upwards towards the mouthpiece duct 5 and towards the side, and thereby breaks through the narrow side wall 17.

On the side facing away from the slide space 21, fin portions 24, which are circular-segment-like when viewed in a horizontal projection towards a narrow side wall 8 and each flank the inner side of the facing wide side walls 8 of the stationary housing part 2', are integrally formed on the slide space wall 23. The radius of these circular-segment-like fin portions 24 substantially corresponds to the size of the vertical extension of the slide space wall 23, a radius line starting approximately from the region of the transition from the slide space wall 23 to the slide space bottom 22. Accordingly, the rim edge, which is in the shape of a portion of a circular curve and is directed substantially upwards, of each fin portion 24 extends into the upwardly pointing rim edge of the slide space wall 23 in a preferably continuous manner. A cover portion 25 is integrally formed in the region of the transition from the fin portion 24 to the slide space wall 23, takes on the curvature of the fin portion on its top side and is directed in the direction of the inner side of the narrow side wall 9 of the stationary housing part 2'.

Guide walls 26, which extend parallel to the wide side walls 16 and are preferably integrally formed and formed of the same material, are arranged within the slide space 21 on the slide space bottom 22. Said guide walls are each provided at an offset from the plane of the associated wide side wall 16, in particular offset by the same amount on both sides with respect to one another, so as to produce a slot-shaped guide between the guide wall 26 and the facing wide side wall 8 of the stationary housing part 2 when the device 1 is in the normal position.

The guide walls 26 support a cover 27 which preferably extends parallel to the slide space bottom 22 and transitions into the aforementioned cover portion 25.

A capsule chamber 28, which is disc-shaped when viewed in a horizontal cross section, is arranged below the cover 27. One part of the circumferential limiting wall thereof is formed by the slide space wall 23 and the rest is formed by a wall 29 suspended from the cover 27.

The capsule chamber 28 opens upwards, passing through the cover 27.

Towards the bottom, the capsule chamber 28 is delimited by a closed chamber bottom 30 which, in the embodiment shown, preferably extends at a vertical distance from the slide space bottom 22.

The diameter of the capsule chamber 28 is preferably selected such that the diameter thereof corresponds to approximately 1.2 to 1.4 times the capsule diameter, so that a capsule 31 inserted into the capsule chamber 28 rests loosely and upright on the chamber bottom 30. More preferably, the vertical height of the capsule chamber 28 corresponds to approximately 1.05 to 1.2 times the length of the capsule.

More preferably, at least when in the normal position, the capsule chamber 28 is arranged as an axial extension of the mouthpiece duct 5, a retaining grating 32 being provided at the bottom of the mouthpiece duct 5, more or less in the junction between the mouthpiece duct 5 and the capsule chamber 28.

The wall 29 of the capsule chamber 28 comprises two vertically superposed guide bushings 33 which are directed towards the plane of the narrow side wall 17. The holes which correspondingly pass through the guide bushings 33 open towards both the narrow side wall 17 and the capsule chamber interior. The bushings 33 are used to guide needles 34, the needle points of which face the capsule chamber interior.

The needles 34 are mounted in needle bearings 35. These needle bearings 35 are formed on a spring-mounted button 36.

The button 36 has a depth which corresponds to the depth of the narrow side wall 17 and a vertical height which corresponds to the free vertical height of the slide space 21.

Counter guide walls 37 are integrally formed on the inside of the button 36 and project into the slide space 21. When viewed in the depth direction of the device 1, said counter guide walls are spaced apart from one another such that they enter the slot-shaped space between the guide wall 26 and the wide side wall 8 of the stationary housing part 2.

An interlocking guide 38 is formed between the faces, which point towards each other, of counter guide walls 37 and the guide wall 26. For this purpose, journals 39, which accordingly face inwards and one another, are integrally formed on the inside of the counter guide walls 37. Said journals engage in groove-like recesses 40 which are formed on the outside of the guide walls 26.

The spring load of the button 36 is achieved by a compression spring 41 supported between the button 36 and the wall 29. Said compression spring accordingly outwardly loads the button 36 in the direction of the narrow side wall 17, said movement direction of the button 36 being limited by a stop by virtue of a web 42 which crosses the recess 40 for the journals 39.

In this case, the limit stop in the interlocking guide 38 is selected such that, when in the normal position loaded by the compression spring, an outwardly directed face of the button 36 is located in the narrow side plane E, thereby accordingly overall forming an extension to or a part of the narrow side wall 17.

A through-flow opening 43, which faces the chamber bottom 30 and opens towards the space 7, is formed in the slide space wall 23. Said opening is preferably arranged such that an airflow sucked in through the opening 43 enters the capsule chamber 28 substantially tangentially.

As a result of the aforementioned configuration of the device, when said device is in the non-use position according to FIG. 1, i.e. also in a storage position, the device has an overall closed shape, more preferably with regard to all the surface planes in particular with no projections. This also offers increased comfort in particular when carrying the device 1 in a pocket close to the body. As a result of this, the button 36 cannot easily be accidentally actuated either, owing to the insertion thereof into the narrow side wall plane E.

When the cap is in the closed position according to FIG. 1, the capsule chamber 28, along with the mouthpiece 4 or the mouthpiece duct 5 and the air inlet opening 15, is also protected against the entry of dirt or the like.

In preparation for an inhalation operation, the housing part 2" is pivoted outwards about the axis y while the device 1 is held in the region of the fixed housing part 2' (cf. FIG. 3). This outwardly pivoted position is preferably limited by a stop, in particular by a rim edge of the bottom part 18 of the pivotable housing part 2" striking a stop block 44 integrally formed on the inside of at least one wide side wall 8.

When the housing part 2" is in this pivoted position, the cover portion 25 covers the free access to the space 7, the integrally formed fin portions 24 also providing guidance of the pivotable housing part 2" in the stationary housing part 2'.

Gripping the pivotable housing part 2" is made easier by window-like cut-out portions 45 which are open towards the narrow side wall 17 and formed in the wide side walls 8 of the stationary housing part 2'. Accordingly, the pivotable housing part 2" can be gripped on either side with two fingers by means of said window-like cut-out portions 45. In this case, the height of the window-like cut-out portions 45 preferably corresponds to the height of the button 36, the width, viewed transverse thereto, of each cut-out portion 45 also being adapted to the possible movement path of the button 36 starting from the rim edge, facing the narrow side wall 17, of the wide side wall 8.

When the housing part 2" is in the outwardly pivoted position, the insert cross section of the capsule chamber 28 is stopped in an acute-angled stop position, preferably assuming an acute angle α of from 30 to 45° relative to the body axis z (also with respect to a longitudinal axis which passes through the centre of the capsule chamber 28).

In this position, the capsule 31 is inserted into the capsule chamber 28, after which the housing part 2" or the receptacle A is moved back into the position in which it enters the housing part 2' at least in part. The result is an inhalation-ready position according to FIG. 4.

In order to carry out the inhalation operation, either before or after the cap 3 is pivoted away to expose the mouthpiece 4 the wall of the capsule 31 is pierced, this taking place as a result of corresponding linear movement of the button 36 counter to the force of the compression spring 41. The needles 34 displaced therewith in the process accordingly pierce the capsule wall. During the movement of the needles 34 towards the capsule chamber 28, said needles pierce the capsule wall, both while the needle points enter the capsule interior and when they exit the capsule interior towards the outside. In this case, the arrangement of the needles 34 is preferably selected such that said needles pierce the capsule 31 in each case for example in the region of the transition from the cylindrical central portion to the cap end portions.

When no more pressure is applied to the button 36 by the user, said button is automatically moved back into the normal position limited by a stop.

For inhaling, the mouthpiece 4 is surrounded by the lips, an air flow (arrow c) being generated thereafter as a result of inhalation. Said air flow enters the space 7 via the air inlet opening 15 and is sucked into the capsule chamber 28 via the through-flow opening 43. At the same time, the air, which passes through the capsule chamber 28 in an eddy-like manner as a result of the preferably tangential inlet, flows through the pierced capsule 31 in order to evacuate the substance 46 stored therein. The air-substance mixture is inhaled via the mouthpiece 6, the capsule 31 or the capsule wall being prevented from being entrained in the air flow by the grating 32.

Advantageously, in particular when the receptacle A or the housing part 2" is in the outwardly pivoted position, good ventilation is provided of the regions through which the suction flow passes, thus in particular the air flow inlet opening 15 and/or the mouthpiece duct 5 and/or the space 7.

LIST OF REFERENCE SIGNS 1 device
2 housing
2' stationary housing part
2" pivotable housing part
3 cap
4 mouthpiece
5 mouthpiece duct
6 mouthpiece outlet
7 space
8 wide side wall
9 narrow side wall
10 bottom-part portion
11 tab
12 recess
13 journal
14 journal socket
15 air inlet opening
16 wide side wall
17 narrow side wall
18 bottom part
19 pivot pin
20 recess
21 slide space
22 slide space bottom
23 slide space wall 24 fin portion
25 cover portion
26 guide wall
27 cover
28 capsule chamber
29 wall
30 chamber bottom
31 capsule
32 retaining grating
33 guide bushing
34 needle
35 needle bearing
36 button
37 counter guide wall
38 interlocking guide
39 journal
40 recess
41 compression spring
42 web
43 through-flow opening
44 stop block
45 cut-away portion
46 substance
c arrow
x pivot axis
y pivot axis
z body axis
A receptacle
E narrow side wall plane
α angle

The invention claimed is:

1. A device for inhaling pulverulent substances contained in capsules, the device comprising:
   a flat, box-shaped housing comprising:
      a first housing part comprising a lower housing part and a mouthpiece, the mouthpiece comprising a mouthpiece duct, the lower housing part comprising:
         a first wide side wall,
         a second wide side wall disposed opposite from the first wide side wall,
         a connecting wall connecting the first wide side wall to the second wide side wall,
         a space between the first wide side wall, the second wide side wall, and the connecting wall and below the mouthpiece duct, and
         a bottom-part portion,
      a receptacle connected to the first housing part via a first pivot pin such that the receptacle is configured to pivot out from the first housing part in a limited manner to an open position about an axis defined by the first pivot pin, the receptacle being disposed in the space of the lower housing part in an unpivoted position, the first pivot pin being disposed in a bottom part of the lower housing part, the receptacle comprising a bottom surface, and
      a spring-mounted button guided in the receptacle and comprising a button face,
      needle bearings connected to the spring-mounted button,
      displaceable needles mounted in the needle bearings, and
      a first stop limiting a movement of the spring-mounted button into the receptacle, and
   a cap connected to the flat, box-shaped housing via a second pivot pin, the cap being configured to rotate about the second pivot pin from a cap open position into a cap closed position, the cap covering the mouthpiece duct in the cap closed position,
   wherein the bottom-part portion of the lower housing part and the bottom surface of the receptacle together form a device bottom surface, the device bottom surface being disposed at a bottom of the device,
   wherein the device has a width, a height, a width-height ratio of 1:2, and a depth, viewed perpendicularly to the height, that corresponds to approximately half of the width,
   wherein the receptacle comprises a capsule chamber, a receptacle narrow outer wall, and a bottom part, the bottom part comprising the first pivot pin,
   wherein in the unpivoted position of the receptacle:
      the mouthpiece duct extends as an axial extension of the capsule chamber, and
      the bottom surface of the receptacle extends straight from the bottom-part portion of the lower housing part,
   wherein the button face and the receptacle narrow outer wall form together a narrow side wall of the flat housing, the button face being formed flush with the receptacle narrow outer wall along the height of the flat housing or being disposed inwards from the receptacle narrow outer wall along the height of the flat housing,
   wherein in the open position:
      the capsule chamber is accessible for insertion of a first capsule into the capsule chamber, and
      the bottom surface of the receptacle extends at an angle from the bottom-part portion of the lower housing part,
   wherein in the unpivoted position of the receptacle, the capsule chamber is in an emptying position such that actuation of the spring-mounted button causes the displaceable needles to pierce a capsule wall of the first capsule in the capsule chamber,
   wherein with respect to a height of the device, the second pivot pin is disposed higher than the first pivot pin, and
   wherein the piercing of the capsule wall allows capsule contents of the first capsule to be evacuated through the mouthpiece duct.

2. The device according to claim 1, further comprising a second stop formed on at least one of the receptacle and the first housing part,
   wherein the second stop stops the pivoting of the receptacle such that in the open position of the receptacle an insert cross section of the capsule chamber is in an acute-angled stop position.

3. The device according to claim 1, wherein the receptacle comprises a groove,
   wherein the spring-mounted button comprises a journal, and
   wherein the journal of the spring-mounted button is guided in the groove of the receptacle.

4. The device according to claim 1, wherein a slide space is formed in the receptacle, and
   wherein the spring-mounted guide button comprises counter guide walls projecting into the slide space.

5. The device according to claim 1, wherein the first wide side wall and the second wide side wall are flat.

* * * * *